US012582630B2

(12) United States Patent
Blackmon et al.

(10) Patent No.: US 12,582,630 B2
(45) Date of Patent: *Mar. 24, 2026

(54) CANNABIS EXTRACTS AND METHODS OF PREPARING AND USING SAME

(71) Applicant: NASCENT PHARMA LLC, Hicksville, NY (US)

(72) Inventors: Earnie Blackmon, Denver, CO (US); Tony Verzura, Denver, CO (US)

(73) Assignee: Nascent Pharma LLC

( * ) Notice: Subject to any disclaimer, the term of this patent is extended or adjusted under 35 U.S.C. 154(b) by 71 days.

This patent is subject to a terminal disclaimer.

(21) Appl. No.: 17/711,548

(22) Filed: Apr. 1, 2022

(65) Prior Publication Data

US 2022/0218657 A1 Jul. 14, 2022

(51) Int. Cl.
| | |
|---|---|
| *A61K 31/353* | (2006.01) |
| *A61K 31/352* | (2006.01) |
| *A61K 36/185* | (2006.01) |

(52) U.S. Cl.
CPC .......... *A61K 31/353* (2013.01); *A61K 31/352* (2013.01); *A61K 36/3482* (2024.05)

(58) Field of Classification Search
CPC .................................................. A61K 31/353
See application file for complete search history.

(56) References Cited

U.S. PATENT DOCUMENTS

| | | | |
|---|---|---|---|
| 2,304,669 | A | 12/1942 | Adams |
| 5,434,295 | A | 7/1995 | Mechoulam et al. |
| 6,013,304 | A | 1/2000 | Todd |
| 6,403,126 | B1 | 6/2002 | Webster et al. |
| 6,630,507 | B1 | 10/2003 | Hampson et al. |
| 6,730,330 | B2 | 5/2004 | Whittle et al. |
| 6,949,582 | B1 | 9/2005 | Wallace |
| 8,846,409 | B2 | 9/2014 | Flockhart et al. |
| 9,549,906 | B2 | 1/2017 | Lynch et al. |
| 9,730,911 | B2 | 8/2017 | Verzura et al. |
| 10,555,928 | B2 * | 2/2020 | Blackmon .............. A61K 31/05 |
| 11,291,650 | B2 * | 4/2022 | Blackmon ............... A61P 25/18 |
| 2003/0017216 | A1 | 1/2003 | Schmidt et al. |
| 2003/0050334 | A1 | 3/2003 | Murty et al. |
| 2004/0033280 | A1 | 2/2004 | Whittle |
| 2004/0049059 | A1 | 3/2004 | Mueller |
| 2004/0138293 | A1 | 7/2004 | Werner et al. |
| 2005/0165088 | A1 | 7/2005 | Whittle et al. |
| 2006/0167283 | A1 | 7/2006 | Flockhart et al. |
| 2008/0057117 | A1 | 3/2008 | Werner et al. |
| 2008/0159961 | A1 | 7/2008 | Woolfe et al. |
| 2010/0035978 | A1 | 2/2010 | Guy et al. |
| 2010/0204312 | A1 | 8/2010 | McAllister et al. |
| 2010/0317729 | A1 | 12/2010 | Guy et al. |
| 2011/0092583 | A1 | 4/2011 | Murty et al. |
| 2011/0230549 | A1 | 9/2011 | Guy et al. |
| 2012/0264818 | A1 | 10/2012 | Newland |
| 2013/0059018 | A1 | 3/2013 | Parolaro et al. |
| 2013/0089600 | A1 | 4/2013 | Winnicki |

| | | | |
|---|---|---|---|
| 2014/0248379 | A1 | 9/2014 | Mueller |
| 2014/0271940 | A1 | 9/2014 | Wurzer |
| 2015/0313868 | A1 | 11/2015 | Morgan |
| 2015/0342902 | A1 | 12/2015 | Vangara et al. |
| 2016/0039591 | A1 | 2/2016 | Kinzer |
| 2016/0081975 | A1 | 3/2016 | Bromley |
| 2016/0279073 | A1 | 9/2016 | Donsky et al. |
| 2016/0324776 | A1 | 11/2016 | Glatzel |

FOREIGN PATENT DOCUMENTS

| | | | |
|---|---|---|---|
| CA | 2 503 310 A1 | 10/2006 | |
| CA | 2 952 858 A1 | 12/2015 | |
| CA | 2 952 994 A1 | 12/2015 | |
| CA | 2 963 202 A1 | 4/2016 | |
| CN | 102246992 A | 11/2011 | |
| DE | 100 51 427 C1 | 6/2002 | |
| EP | 2 182 940 B1 | 3/2014 | |
| GB | 2 400 319 A | 10/2004 | |
| GB | 2 434 312 A | 7/2007 | |
| JP | 2004-511517 | 4/2004 | |
| JP | 2010-524912 A | 7/2010 | |
| WO | WO 02/32420 A1 | 4/2002 | |
| WO | WO 02/064109 A2 | 8/2002 | |
| WO | WO 2004/016246 A1 | 2/2004 | |
| WO | WO 2004/016277 A2 | 2/2004 | |
| WO | WO 2005/120478 A1 | 12/2005 | |
| WO | WO 2008/129258 A1 | 10/2008 | |
| WO | WO 2009/007697 A1 | 1/2009 | |
| WO | WO 2013/057487 A1 | 4/2013 | |

(Continued)

OTHER PUBLICATIONS

A.C.T. Now Diagnostics Pamphlet, www.unitedcannabis.US/wp-content/uploads/2014/04/ACTNOW_Diagnostics_Prana_Guide.pdf, 3 pages.

Aizpurua-Olaizola, O. et al., "Evolution of the Cannabinoid and Terpene Content during the Growth of Cannabis sativa Plants from Different Chemotypes," J. Nat. Prod., 79:324-331 (2016).

Alice O'Leary-Randall, Denver—Sanity Prevails, aliceolearyrandall.wordpress.com/2014/05/01/denver-sanity-prevails, 2 pages.

Andre, C. M. et al., "Cannabis sativa: The Plant of the Thousand and One Molecules," Frontiers in Plant Science, 7:19. Published Feb. 4, 2016. doi:10.3389/fpls.2016.00019 (2016).

(Continued)

*Primary Examiner* — Rei Tsang Shiao

(74) *Attorney, Agent, or Firm* — Sigma Law Group LLC; James Smedley; Alex Korona

(57) ABSTRACT

The invention relates to the extraction of pharmaceutically active components from plant materials, and more particularly to the preparation of a botanical drug substance (BDS) for incorporation in to a medicament. It also relates to a BDS, for use in pharmaceutical formulations. In particular it relates to BDS comprising cannabinoids obtained by extraction from *Cannabis*.

15 Claims, No Drawings

(56) References Cited

FOREIGN PATENT DOCUMENTS

| WO | WO 2013/165251 A1 | 11/2013 |
|----|----|----|
| WO | WO 2013/169101 A1 | 11/2013 |
| WO | WO 2014/100231 A1 | 6/2014 |
| WO | WO 2014/134281 A1 | 9/2014 |
| WO | WO 2015/193668 A1 | 12/2015 |

OTHER PUBLICATIONS

Appendix A to Pure Hemp's Invalidity Contentions—Anticipation Invalidity Contention Claim Chart for U.S. Pat. No. 9,730,911, Case 1:18-cv-01922, *United Cannabis Corporation* v. *Pure Hemp Collective Inc.*, USDC Colorado, Jan. 8, 2019, 80 pages.

Appendix B to Pure Hemp's Invalidity Contentions—Obviousness Invalidity Contention Claim Chart for U.S. Pat. No. 9,730,911; Case 1:18-cv-01922, *United Cannabis Corporation* v. *Pure Hemp Collective Inc.*, USDC Colorado, Jan. 8, 2019, 13 pages.

Appendix C to Pure Hemp's Invalidity Contentions—Other Invalidity Contentions Claim Chart for U.S. Pat. No. 9,730,911, Case 1:18-cv-01922, *United Cannabis Corporation* v. *Pure Hemp Collective Inc.*, USDC Colorado, Jan. 8, 2019, 8 pages.

Baker, D. et al., "Cannabinoids control spasticity and tremor in a multiple sclerosis model," Nature, 404:84-87 (2000).

Bodwin, E. "A drug derived from marijuana has become the first to win federal approval, and experts predict an avalanche effect," businesinsider.com/marijuana-epilepsy-drug-approved-fda-2018-5, Jun. 25, 2018, 10 pages.

Booth, J. K. et al., "Terpene synthases from Cannabis sativa," PLOS One, online doi.org/10.1371/journal.pone.0173911, Mar. 29, 2017, 20 pages.

Briefing on Supplemental Authority, dated Jan. 22, 2019, filed Jan. 22, 2019, Case 1:18-cv-01922, *United Cannabis Corporation* v. *Pure Hemp Collective Inc.*, USDC Colorado, 7 pages.

Calixto, J. B. et al., "Naturally Occurring Antinociceptive Substances from Plants," Phytother. Res., 14:401-418 (2000).

Cannabinoid, from Wikipedia, en.wikipedia.org/w/index.php?title=Cannabinoid&oldid=630426170, 2014, 15 pages.

Complaint for Patent Infringement and Demand for Jury Trial, filed Jul. 30, 2018, Case 1:18-cv-01922, *United Cannabis Corporation* v. *Pure Hemp Collective Inc.*, USDC Colorado, 10 pages.

Database WPI, Week 201215, Thomson Scientific, CN 102246992A, Nov. 23, 2011, 2 pages.

Dayanandan, P. & Kaufman, P. B., "Trichomes of *Cannabis sativa* L. (Cannabaceae)," Amer. J. Bot., 63(5):578-591 (1976).

Declaration of Brent Reynolds, executed on Dec. 28, 2018, 7 pages.

Declaration of James Gourley in Support of Defendant's Early Motion for Partial Summary Judgment, filed Nov. 29, 2018, Case 1:18-cv-01922, *United Cannabis Corporation* v. *Pure Hemp Collective Inc.*, USDC Colorado, 4 pages.

Declaration of James R. Gourley in Support of Pure Hemp's Opposition to UCANN's Motion to Correct Claim 31, filed Jan. 19, 2019, Case 1:18-cv-01922, *United Cannabis Corporation* v. *Pure Hemp Collective Inc.*, USDC Colorado, 4 pages.

Declaration of Tony Verzura, executed on Dec. 21, 2018, 9 pages.

Defendant's Answer, Defenses, and Counterclaims, filed Oct. 29, 2018, Case 1:18-cv-01922, *United Cannabis Corporation* v. *Pure Hemp Collective Inc.*, USDC Colorado, 15 pages.

Defendant's Early Motion for Partial Summary Judgment, filed Nov. 29, 2018, Case 1:18-cv-01922, *United Cannabis Corporation* v. *Pure Hemp Collective Inc.*, USDC Colorado, 17 pages.

Defendant's First Amended Answer, Defenses, and Counterclaims, filed Nov. 5, 2018, Case 1:18-cv-01922, *United Cannabis Corporation* v. *Pure Hemp Collective Inc.*, USDC Colorado, 17 pages.

Defendant's First Amended Answer, Defenses, and Counterclaims, CORRECTED, filed Nov. 5, 2018, Case 1:18-cv-01922, *United Cannabis Corporation* v. *Pure Hemp Collective Inc.*, USDC Colorado, 17 pages.

Defendant's First Requests for Production to Plaintiff United Cannabis Corporation dated Nov. 8, 2018, Case 1:18-cv-01922, *United Cannabis Corporation* v. *Pure Hemp Collective Inc.*, USDC Colorado, 10 pages.

Defendant's Initial Disclosure Statement dated Nov. 16, 2018, Case 1:18-cv-01922, Case 1:18-cv- 01922, *United Cannabis Corporation* v. *Pure Hemp Collective Inc.*, USDC Colorado, 5 pages.

Defendant's Objections and Responses to Plaintiff's First Interrogatories dated Dec. 12, 2018, Case 1:18-cv-01922, *United Cannabis Corporation* v. *Pure Hemp Collective Inc.*, USDC Colorado, 10 pages.

Defendant's Objections and Responses to Plaintiff's First Requests for Production dated Dec. 10, 2018, Case 1:18-cv-01922, *United Cannabis Corporation* v. *Pure Hemp Collective Inc.*, USDC Colorado, 18 pages.

Defendant's Objections and Responses to Plaintiff's Second Requests for Production dated Feb. 8, 2019, Case 1:18-cv-01922, *United Cannabis Corporation* v. *Pure Hemp Collective Inc.*, USDC Colorado, 6 pages.

Defendant's Second Requests for Production to Plaintiff United Cannabis Corporation dated Dec. 10, 2018, Case 1:18-cv-01922, *United Cannabis Corporation* v. *Pure Hemp Collective Inc.*, USDC Colorado, 7 pages.

Devinsky, O. et al., "Cannabidiol: Pharmacology and potential therapeutic role in epilepsy and other neuropsychiatric disorders," Epilepsia, 55(6):791-802 (2014).

Dmitrieva, N. et al., "Endocannabinoid involvement in endometriosis," PAIN, 151:703-710 (2010).

Down At RiverRock—Colorado's Largest Dispensary, sensiseeds.com/en/blog/riverrock-colorados-largest-dispensary/, Jun. 26, 2014.

Draper, W. A Son's Story—Hemp Connoisseur Magazine, www.hcmagazine.com/a-sons-story/, Feb. 5, 2014, 3 pages.

Elsohly, M. A. & Slade, D., "Chemical constituents of marijuana: The complex mixture of natural cannabinoids," Life Sciences, 78:539-548 (2005).

Fagron, Inc. THC Material Data Safety Sheet, printing date Jul. 29, 2014, Version 23, 8 pages.

FDA Briefing Document, Peripheral and Central Nervous System Drugs, Advisory Committee Meeting, NDA 210365, Cannabidiol, Apr. 19, 2018, 64 pages; www.fda.gov/downloads/advisorycommittees/committeesmeetingmaterials/-drugs/peripheral and central nervous system drugs advisorycommittee/ucm604736.pdf.

Goldman, B., "Blocking brain's 'internal marijuana' may trigger early Alzheimer's deficits, study shows," Jun. 2014, med.stanford.edu/news/all-news/2014/06/blocking-brain_s-internal-marijuana-may-trigger-early-alzheimers.html, 3 pages.

Grotenhermen, F., "Pharmacokinetics and Pharmacodynamics of Cannabinoids," Clin Pharmacokinet, 42(4):327-360 (2003).

Gul, W. et al., "Determination of 11 Cannabinoids in Biomass and Extracts of Different Varieties of Cannabis Using High-Performance Liquid Chromatography," Journal of AOAC International, 98(6):1523-1528 (2015).

Harte-Hargrove, L. C. & Dow-Edwards, D. L., "Withdrawal from THC during adolescence: Sex differences in locomotor activity and anxiety," Behavioural Brain Research, 231:48-59 (2012).

Hill, M. N. et al., "Functional Interactions between Stress and the Endocannabinoid System: From Synaptic Signaling to Behavioral Output," The Journal of Neuroscience, 30(45): 14980-14986 (2010).

IUPAC Gold Book Entry: resin; goldbook.iupac.org/RT07166.html, (2006), 3 pages.

Izzo, A. A. & Coutts, A. A., "Cannabinoids and the Digestive Tract," Handb Exp Pharmacol., 168:573-598 (2005).

Joint Disputed Claim Chart dated Apr. 16, 2019, Case 1:18-cv-01922, *United Cannabis Corporation* v. *Pure Hemp Collective Inc.*, USDC Colorado, 4 pages.

Kurz, R. & Blaas, K., "Use of dronabinol (delta-9-THC) in autism: A prospective single-case-study with an early infantile autistic child," Cannabinoids, 5(4):4-6 (2010).

Medvinskii, L. A. & Kolesnichenko, T. S., "Modification of the "Hanging Drop" Method for Culturing Reaggregates of Dissociated Cells and Explants of Embryonic Lung," Bulletin of Experimental Biology and Medicine, Mar. 1981, vol. 91, Issue 3, pp. 408-410.

(56)          References Cited

OTHER PUBLICATIONS

Meir Medical Center. NCT1037322 Clinical Trial "Cannabidiol for Inflammatory Bowel Disease." clinicaltrials.gov/ct2/show/NCT01037322, 2009, 5 pages.

Naftali, T et al., "Cannabis Induces a Clinical Response in Patients With Crohn's Disease: A Prospective Placebo-Controlled Study," Clinical Gastroenterology and Hepatology, 11:1276-1280 (2013), and Supplementary Fig. 1, 1 page.

Notice of Supplemental Authority dated Apr. 17, 2019, Case 1:18-cv-01922, *United Cannabis Corporation* v. *Pure Hemp Collective Inc.*, USDC Colorado, 3 pages.

Ohlsson, A. et al., "Plasma delta-9-tetrahydrocannabinol concentrations and clinical effects after oral and intravenous administration and smoking," Clin Pharmacol Ther, 28(3):409-16 (1980).

Ohlsson, A. et al., "Single-dose Kinetics of Deuterium-labelled Cannaboidiol in Man After Smoking and Intravenous Administration," Biomedical and Environmental Mass Spectrometry, 13:77-83 (1986).

Order Denying Defendant's Early Motion for Partial Summary Judgment dated Apr. 17, 2019, Case 1:18-cv-01922, *United Cannabis Corporation* v. *Pure Hemp Collective Inc.*, USDC Colorado, 16 pages.

Past Winners—Cannabis Cup, River Rock, 2012, www.cannabiscup.com/past-winners/#denver, 1 page.

Past Winners—Cannabis Cup, www.cannabiscup.com/past-winners/#denver-, 2015, 11 pages.

Perez-Reyes et al., "Pharmacology of orally administered Delta9-tetrahydrocannabinol," Clin Pharmacol Ther., 14(1):48-559 (1973).

Pertwee, R. G., "Cannabinoid pharmacology: the first 66 years," British Journal of Pharmacology, S163-S171 (2006).

Plaintiff United Cannabis Corporation's Initial Disclosures Under Fed. R. Civ. P. 26(a), dated Nov. 16, 2018, Case 1:18-cv-01922, *United Cannabis Corporation* v. *Pure Hemp Collective Inc.*, USDC Colorado, 6 pages.

Plaintiff's Motion to Correct Claim 31 of U.S. Pat. No. 9,730,911, filed Dec. 31, 2018, Case 1:18-cv-01922, *United Cannabis Corporation* v. *Pure Hemp Collective Inc.*, USDC Colorado, 8 pages.

Pouton, C. W. & Porter, C. J. H., "Formulation of lipid-based delivery systems for oral administration: Materials, methods and strategies," Advanced Drug Delivery Reviews, 60:625-637 (2008).

Pure Hemp Collective CBD products. purehempcollective.com/ (Jul. 20, 2017), 6 pages.

Pure Hemp Collective, Tincture Product Page. purehempcollective.com/product/tinture, 11/27, 2018, 4 pages.

Pure Hemp's List of Claim Terms to be Construed for U.S. Pat. No. 9,730,911, Certificate of Service to counsel by email dated Mar. 19, 2019, 1 page.

Pure Hemp's Amended List of Claim Terms to be Construed for U.S. Pat. No. 9,730,911, Certificate of Service to counsel by email dated Apr. 3, 2019, 1 page.

Pure Hemp's Answer, Defenses, and Counterclaims to UCANN's First Amended Complaint dated Apr. 12, 2019, with accompanying Exhibits A-D, Case 1:18-cv-01922, *United Cannabis Corporation* v. *Pure Hemp Collective Inc.*, USDC Colorado, 54 pages.

Pure Hemp's Claim Construction Reply Brief dated Jun. 14, 2019, Case 1:18-cv-01922, *United Cannabis Corporation* v. *Pure Hemp Collective Inc.*, USDC Colorado, 12 pages.

Pure Hemp's Invalidity Contentions, dated Jan. 8, 2019, Case 1:18-cv-01922, *United Cannabis Corporation* v. *Pure Hemp Collective Inc.*, USCD Colorado, 6 pages.

Pure Hemp's Opposed Motion for leave to Brief the Invalidity of Certificate of Correction for U.S. Pat. No. 9,730,911 in Conjunction with Claim Construction dated Apr. 29, 2019, Case 1:18-cv-01922, *United Cannabis Corporation* v. *Pure Hemp Collective Inc.*, USDC Colorado, 6 pages.

Pure Hemp's Opposition to UCANN's Motion to Correct Claim 31, filed Jan. 19, 2019, Case 1:18-cv-01922, *United Cannabis Corporation* v. *Pure Hemp Collective Inc.*, USDC Colorado, 14 pages.

Pure Hemp's Response to UCANN's Briefing on Supplemental Authority, dated Jan. 22, 2019, filed Jan. 22, 2019, Case 1:18-cv-01922, *United Cannabis Corporation* v. *Pure Hemp Collective Inc.*, USDC Colorado, 7 pages.

Pure Hemp's Responses to UCANN's Invalidity Contentions dated Jan. 8, 2019, Case 1:18-cv-01922, *United Cannabis Corporation* v. *Pure Hemp Collective Inc.*, USDC Colorado, 7 pages.

Reply Brief in Support of Defendant's Early Motion for Partial Summary Judgment, filed Jan. 14, 2019, Case 1:18-cv-01922, *United Cannabis Corporation* v. *Pure Hemp Collective Inc.*, USDC Colorado, 14 pages.

Russo, E., "Cannabis in acute migraine treatment project: Response to National Institutes of Health Critique," Newsletter of the Multidisciplinary Association for Psychedelic Studies, 8(1): 15-17 (1998); www.maps.org/news-letters/v08n1/08115rus.html.

Russo, E. B., "Taming THC: potential cannabis synergy and phytocannabinoid-terpenoid entourage effects," British Journal of Pharmacology, 163:1344-1364 (2011).

Shi Jinzhu, "Medium Chain Triglyceride and Application Thereof", Shanxi Grain and Oil Science and Technology, vol. 17, No. 51, pp. 32-34 (1991), with machine English translation.

Smith, S. C. & Wagner, M. S., "Clinical endocannabinoid deficiency (CECD) revisited: Can this concept explain the therapeutic benefits of cannabis in migraine, fibromyalgia, irritable bowel syndrome and other treatment-resistant conditions?," Neuroendocrinology Letters, 35(3): 198-201 (2014).

Stepan S. Lipid Nutrition. Neobee® Medium Chain Triglycerides, Product Brochure, 2012, 6 pages.

The Pharmacopoeia of the United States of America, Four Decennial Revision, published 1864, 15 pages.

Tocris. Certificate of Analysis for CBN, print date Jun. 29, 2018, 3 pages.

Tocris. Certificate of Analysis for CBD, print date Jun. 29, 2018, 3 pages.

Tramèr, M. R et al., "Cannabinoids for control of chemotherapy induced nausea and vomiting: quantitative systematic review," BMJ, 323:1-8 (2001).

Unimed Pharmaceuticals, Inc. Company. Marinol® (Drabinol) Product Description, 2012, 12 pages.

United Cannabis Corporation's Answer to Pure Hemp Collective Inc.'s First Amended Answer, Defenses, and Counterclaims, filed Nov. 19, 2018, Case 1:18-cv-01922, *United Cannabis Corporation* v. *Pure Hemp Collective Inc.*, USDC Colorado, 8 pages.

United Cannabis Corporation's Infringement Contentions dated Nov. 27, 2018, 20 pages.

United Cannabis Corporation's Opposition Brief to Pure Hemp Collective Inc.'s Early Motion for Partial Summary Judgment filed Dec. 31, 2018, Case 1:18-cv-01922, *United Cannabis Corporation* v. *Pure Hemp Collective Inc.*, USDC Colorado, 22 pages.

Van Laere, K. et al., "Regional changes in type 1 cannabinoid receptor availability in Parkinson's disease in vivo," Neurobiology of Aging, 33:620.e1-620.e8 (2012); doi: 10.1016/j.neurobiolaging.2011.02.009. Epub Apr. 2, 2011.

Wall, M. E. et al., "Metabolism, disposition, and kinetics of delta-9-tetrahydrocannabinol in men and women," Clin. Pharmacol. Ther., 34(3):352-363 (1983).

Wallace, M. J. et al., "The Endogenous Cannabinoid System Regulates Seizure Frequency and Duration in a Model of Temporal Lobe Epilepsy," The Journal of Pharmacology and Experimental Therapeutics, 307(1): 129-137 (2003).

Wang, M. et al., "Decarboxylation Study of Acidic Cannabinoids: A Novel Approach Using Ultra-High-Performance Supercritical Fluid Chromatography/Photodiode Array-Mass Spectrometry," Cannabis and Cannabinoid Research, 1(1):262-271 (2016).

Wayback Machine Archive from DixiX website. Dixie X Dew Drops, Hemp Oil Tincture; <web.archive.org/web/20121118204038/http://dixiex.com:80/index.php/dixie-x-dew-drops>, 2 pages.

Wayback Machine Archive from DixiX website. Dixie X FAQ; dixiex.com:80/index.php/faq, 2012, 1 page.

Wayback Machine Archive from Echo Pharmaceuticals website, Oct. 2011; www.echo-pharma.com/en/products-and-pipeline/cannabinoid-standards/, 1 page.

(56) References Cited

OTHER PUBLICATIONS

Wayback Machine Archive from Tocris Bioscience website, Apr. 2013; www.tocris.com/dispprod.php?ItemId=46925, 2 pages.

Yamamoto, I., "Why is hemp sacred," Chemistry, 64(5):31-37 (2009).

* cited by examiner

CANNABIS EXTRACTS AND METHODS OF PREPARING AND USING SAME

RELATED APPLICATIONS

This application is continuation of U.S. patent application Ser. No. 16/717,914, filed Dec. 17, 2019, which is a continuation of U.S. patent application Ser. No. 15/676,407, filed on Aug. 14, 2017, now U.S. Pat. No. 10,555,928, which is a divisional of U.S. patent application Ser. No. 14/919, 245, filed Oct. 21, 2015, now U.S. Pat. No. 9,730,911, and claims priority to and the benefit of U.S. Provisional Application No. 62/066,795 filed on Oct. 21, 2014 and U.S. Provisional Application No. 62/068,278 filed on Oct. 24, 2014, the contents of each of which are incorporated by reference in their entireties.

FIELD OF THE INVENTION

This invention relates to the extraction of pharmaceutically active components from plant materials, and more particularly to botanical drug substance (BDS) comprising cannabinoids obtained by extraction from *Cannabis*. Methods of using the extracts to treat chronic pain, paralysis, neuropathy, Crohn's Disease, IBS, glaucoma, PTSD, anxiety, seizures, epilepsy, autoimmune disorders autism, tumors, and cancer are also included.

BACKGROUND OF THE INVENTION

*Cannabis* products have been consumed in various forms for thousands of years. The first descriptions of the medical uses date from Chinese herbal texts in the first century A.D. *Cannabis* products were taken orally in an herbal tea concoction and were used for their pain-relieving and sleep-inducing properties.

There presently exists the need to provide more effective and safer *Cannabis* extracts for various medical uses, extraction methods that provide unique active compounds that are useful to treat pain and various medical conditions. Additionally, presently known extraction procedures do not provide the desired active ingredient(s) for the particular medical purpose. The present invention overcomes these limitations and provides other related advantages.

SUMMARY OF THE INVENTION

The invention provides an extract comprising a mixture of at least 95% total cannabinoids, and at least one terpene/ flavonoid. The extract contains at least 4, 5, 6, 7 or more cannabinoids. The cannabinoids are selected from tetrahydrocannabinolic acid (THCa), cannabidiolic acid (CBDa), cannabinolic acid (CBNa) cannabichromenic acid (CBCa), tetrahydrocannabinol (THC), cannabinol (CBN), cannabidiol (CBD) or cannabichromene (CBC). In some aspect the cannabinoids are THCa and CBDa and at least two cannabinoids selected from CBNa, CBCa, THC, CBN and CBC. In a preferred embodiment the cannabinoids are THC, CBN, CBC and CBD. In another preferred embodiment the cannabinoids are THCa, CBDa, CBNa and CBCa. In yet another preferred embodiment the cannabinoids are THCa, CBDa, THC, CBN, and CBC.

The terpene/flavonoid is for example, d-limonene linalool, 1,8-cineole (eucalyptol), α-pinene, terpineol-4-ol, p-cymene, borneol, Δ-3-carene, β-sitosterol, β-myrcene, or β-caryophyllene.cannflavin A, apigenin, quercetin or pulegone.

Also provided by the invention are formulations containing the extracts according to the invention. For example the formulation contains any of the extracts according to the invention infused with a medium chain triglyceride (MCT). The MCT is for example, NEOBEE 895.

Preferably, the pH of the formulation is at least pH 8.0.

In some formulations the concentration of THCa is greater than or equal to 95%; CBDa is less than 1%; CBNa is less than 3%; and CBCa is less than 1%. Optionally the formulation further contains d-limonene, linalool, 1,8-cineole (eucalyptol), α-pinene, terpineol-4-ol, p-cymene, borneol, Δ-3-carene, β-sitosterol, cannflavin A, apigenin, quercetin In other formulations the concentration of THCa is less than or equal to 35%; CBDa is greater than or equal to 60%; THC is less than 1%; CBN is less than 1%; and CBC is less than 1%. Optionally, the formulation further contains d-limonene, linalool, 1,8-cineole (eucalyptol), α-pinene, terpineol-4-ol, p-cymene, borneol, Δ-3-carene, β-sitosterol, cannflavin A, apigenin, quercetin In another formulation the concentration of THCa is greater than or equal to 40%;CBDa is greater than or equal to 40%; THC is less than 1%; CBN is less than 1%; and CBC is less than 1%. Optionally, the formulation further conatains β-myrcene, β-caryophyllene, pulegone, α-terpineol, β-sitosterol, cannflavin A, apigenin, quercetin In yet another formulation the concentration of THC is less than or equal to 9%; CBD is greater than or equal to 40%; CBN is greater than or equal to 40%; and CBS is less than 1%. Optionally, the formulation further contains β-myrcene, β-caryophyllene, pulegone, α-terpineol, β-sitosterol, cannflavin A, apigenin, quercetin.

In various aspects the formulation of the invention are formulated for r oral, sublingual, buccal, or topical administration. The sublingual formulation further contains a sweetener such as a *stevia* extract. Optionally, the sublingual formulation further contains lemon oil, orange oil or both.

In other aspects the invention provides a method of preparing a *Cannabis* extract providing fresh or live *Cannabis* plant material; extracting the cannabinoids from the plant material to produce a first extract; winterizing and purging the winterized extract. Optionally, the method further incudes decarboxylating the phytocannabinoids prior to extraction. The decarboxylation is accomplished for example, by heating the dried plant material at a temperature of about 221° F. for at least 15 minutes followed by heating at about 284° F. for at least 45 minutes. In some aspects the winterized extract is heated at 284° F. for about 45-74 minutes followed by heating at about 293° F. for at least about 55-90 minutes.

Extraction is for example by hydrocarbon extraction. Winterizing includes adding cold ethanol to the first extract or storing the first extract at a temperature of about −20° to about −75° F. for about 48 hours to produce a waxy precipitate and removing the waxy precipitate by filtration. Optionally, the winterized extract is filtered through activated charcoal.

The *Cannabis* plant material consists of flowers or flowers and leaves. In some aspects the *Cannabis* plant material is frozen at a temperature between at least −10° F. to −50° F. for at least 36 hours prior to being extracted. Preferably, the *Cannabis* plant material has been propagated from a single seed source or a tissue culture with specific ratios of cannabinoids. In some aspects the *Cannabis* plant material is derived from a *Cannabis* strain having a minimum of 15% THC and less that 1% CBD. In others aspect the *Cannabis* plant material is derived from Sour Tsunami×Catatonic Sour TsunamixSour Tsunami, Sour Tsunami, Harlequin, R4 ACDC strains. In yet other as aspects the *Cannabis* plant material is derived from CBD1, Sour Pineapple, CBD Diesel, Harlequin, ACDC or R4. In yet a further aspect the *Cannabis* plant material is derived from Sour Tsunamix Catatonic, Sour TsunamixSour Tsunami, Sour Tsunami, Harlequin, R4, Swiss Gold, ACDC, CBD1, Sour Pineapple, or CBD Diesel.

The invention further provides a method for preparing *Cannabis* juice by blanching fresh *Cannabis* leaves obtained from a *Cannabis* plant in the vegetative stage in cold water; juicing the leaves in a cold press juicer or masticating juicer; and filtering the juice through a filter to remove particulates. Optionally, filter juice is freeze dried.

The juicer is for example, a cold press juicer or a masticating juicer. Also included in the invention is juice produced according to the method of the invention. In some embodiments the *Cannabis* juice is obtained from *Cannabis* flowers, *Cannabis* roots or both.

The invention also provides method of relieving symptoms associated with anxiety, post traumatic stress disorder, chronic pain, or opiate dependency, paralysis, neuropathy, Crohns disease, inflammatory bowel disorders, glaucoma, seizures, epilepsy, autism, or cancer comprising administering to a subject in need thereof one or more of the formulations or juice according to the invention. The formulations are administered four times daily. For example the formulation is administered in the morning; afternoon, evening and at bedtime.

In specific embodiments the invention provides a method of treating cancer by administering to a subject a total daily doses of: 20 mg of cannabinoid extract and 50 mg of raw *Cannabis* juice for seven days; 40 mg of cannabinoid extract and 50 mg of raw *Cannabis* juice for seven days; 80 mg of cannabinoid extract and 50 mg of raw *Cannabis* juice for seven days; 120 mg of cannabinoid extract and 50 mg of raw *Cannabis* juice for seven days; and 160 mg of cannabinoid extract and 100 mg of raw *Cannabis* juice for seven days. In some aspects the method further includes administering a total daily dose of 200 mg cannabinoid extract and 100 mg of raw *Cannabis* juice every day thereafter or administering 200 mg of cannabinoid extract and 100 mg of raw *Cannabis* juice for seven days; and 400 mg of cannabinoid extract and 100 mg of raw *Cannabis* juice every day thereafter.

In another embodiment the invention provides method of treating opioid dependency by reducing the amount of opiates used per day by at least 10% and administering to a subject a total daily doses of: 31 mg of cannabinoid extract and 50 mg of raw *Cannabis* for fourteen days; 56 mg of cannabinoid extract and 50 mg of raw *Cannabis* for fourteen days; 84 mg of cannabinoid extract and 50 mg of raw *Cannabis* juice for fourteen days; 104 mg of cannabinoid extract and 50 mg of raw *Cannabis* for fourteen days; 89 mg of cannabinoid extract and 50 mg of raw *Cannabis* for fourteen days; 69 mg of cannabinoid extract and 50 mg of raw *Cannabis* for fourteen days; 49 mg of cannabinoid extract and 50 mg of raw *Cannabis* for fourteen days; and 41 mg of cannabinoid extract and 50 mg of raw *Cannabis* for fourteen days.

Optionally, the method further includes administering a total daily dose of 36 mg cannabinoid extract and 25 mg of raw *Cannabis* every day thereafter and a single dose of 50 mg raw *Cannabis* every three days.

In another embodiment, the invention provides a method of treating anxiety/PTSD by administering to a subject a total daily doses of about 28 mg to 42 mg of cannabinoid extract.

In a further embodiment, the invention includes a method of treating chronic pain by administering to a subject a total daily doses of about 36 mg to 48 mg of cannabinoid extract.

The formulations are administered four times daily. For example, the formulation is administered in the morning; afternoon, evening and at bedtime.

Other features and advantages of the invention will be apparent from and are encompassed by the following detailed description and claims.

DETAILED DESCRIPTION

The present invention is based in part upon extraction procedures and delivery approaches that allow selective utilization of various cannabinoid molecules and terpenes from the whole *Cannabis Sativa* plant. These various cannabinoid compounds are designed to selectively affect various cannabinoid receptors in the nervous system, immune system and other tissues. The extract is an oil-based whole plant product that contains inactive and active compounds contained in the *Cannabis* plant such as cannabinoids, terpenes and/or flavonoids. Compositions of the invention and methods of extraction disclosed herein provide an extract with specific physiological properties that are mediated through separate pathways and receptors, which provide numerous benefits and advantages.

The extracts and/or delivery methods of the invention allows a wide range of prevention, treatment and management options for patients. In some aspects the delivery methods of the invention employs micro-dosing with a stacking method of cannabinoid administration week by week until a certain saturation point that is based on response, weight, and monthly-quarterly test results.

Surprisingly, it was discovered that the age or the *Cannabis* plant material, the temperature in which it is stored and processed is critical and the ratio of the specific cannabinoids extract is critical to effectiveness of the final formulation. Importantly, for an extract to maintain non-psychoactive properties the *Cannabis* plant material is never heated above 160° F. Preferably, the non-psychoactive extracts according to the invention are formulated at 110° F. or below.

*Cannabis* is a genus of flowering plants that includes three different species, *Cannabis sativa, Cannabis* indica and *Cannabis ruderalis*. The term "*Cannabis* plant(s)" encompasses wild type *Cannabis* and also variants thereof, including *Cannabis* chemovars which naturally contain different amounts of the individual cannabinoids. For example, some *Cannabis* strains have been bred to produce minimal levels of THC, the principal psychoactive constituent responsible for the high associated with it and other strains have been selectively bred to produce high levels of THC and other psychoactive cannabinoids.

*Cannabis* plants produce a unique family of terpeno-phenolic compounds called cannabinoids, which produce the "high" one experiences from consuming marijuana. There are 483 identifiable chemical constituents known to exist in the *Cannabis* plant, and at least 85 different cannabinoids have been isolated from the plant. The two cannabinoids usually produced in greatest abundance are cannabidiol (CBD) and/or Δ9-tetrahydrocannabinol (THC), but only THC is psychoactive. *Cannabis* plants are categorized by their chemical phenotype or "chemotype," based on the overall amount of THC produced, and on the ratio of THC to CBD. Although overall cannabinoid production is influenced by environmental factors, the THC/CBD ratio is genetically determined and remains fixed throughout the life of a plant. Non-drug plants produce relatively low levels of THC and high levels of CBD, while drug plants produce high levels of THC and low levels of CBD.

The best studied cannabinoids include tetrahydrocannabinol (THC), cannabidiol (CBD) and cannabinol (CBN). Other cannabinoids include for example, cannabichromene (CBC), cannabigerol (CBG) cannabinidiol (CBND), Cannabicyclol (CBL), Cannabivarin (CBV), Tetrahydrocannabivarin (THCV), Cannabidivarin (CBDV), Cannabichromevarin (CBCV) Cannabigerovarin (CBGV),Cannabigerol Monomethyl Ether (CBGM).

Cannabinoids are derived from their respective 2-carboxylic acids (2-COOH) by decarboxylation (catalyzed by heat, light, or alkaline conditions). As a general rule, the carboxylic acids form of the cannabinoid have the function of a biosynthetic precursor.

As used herein THC, CBD, CBN, CBC, CBG, CBND, CBL, CBV, THCV, CBDV, CBCV, CBGV and CBGM refer to the decarboxylated form of the cannabinoid. Whereas, THCa, CBDa, CBNa, CBCa, CBGa, CBNDa, CBLa, CBVa, THCVa, CBDVa, CBCVa, CBGVa and CBGM refer to the acid form of the cannabinoid.

Tetrahydrocannabinol (THC) is the primary psychoactive component of the *Cannabis* plant. THC is only psychoactive in is decarboxylated state. The carboxylic acid form (THCa) is non-psychoactive.

Delta-9-tetrahydrocannabinol (Δ9-THC, THC) and delta-8-tetrahydrocannabinol (Δ8-THC), mimic the action of anandamide, a neurotransmitter produced naturally in the body. These two THCs produce the effects associated with *Cannabis* by binding to the CB1 cannabinoid receptors in the brain. THC appears to ease moderate pain (analgesic) and to be neuroprotective, while also offering the potential to reduce neuroinflammation and to stimulate neurogenesis. THC has approximately equal affinity for the CB1 and CB2 receptors.

Cannabidiol (CBD) is not psychoactive, and was thought not to affect the psychoactivity of THC. However, recent evidence shows that smokers of *Cannabis* with a higher CBD/THC ratio were less likely to experience schizophrenia-like symptoms.[15] This is supported by psychological tests, in which participants experience less intense psychotic-like effects when intravenous THC was co-administered with CBD (as measured with a PANSS test). Cannabidiol has little affinity for CB1 and CB2 receptors but acts as an indirect antagonist of cannabinoid agonists. Recently it was found to be an antagonist at the putative new cannabinoid receptor, GPR55, a GPCR expressed in the caudate nucleus and putamen. Cannabidiol has also been shown to act as a 5-HT1A receptor agonist, an action that is involved in its antidepressant, anxiolytic, and neuroprotective effects.

It appears to relieve convulsion, inflammation, anxiety, and nausea. CBD has a greater affinity for the CB2 receptor than for the CB1 receptor. CBD shares a precursor with THC and is the main cannabinoid in low-THC *Cannabis* strains. CBD apparently plays a role in preventing the short-term memory loss associated with THC in mammals.

Cannabinol (CBN) is the primary product of THC degradation, and there is usually little of it in a fresh plant. CBN content increases as THC degrades in storage, and with exposure to light and air. It is only mildly psychoactive. Its affinity to the CB2 receptor is higher than for the CB1 receptor Cannabigerol (CBG) is non-psychotomimetic but still affects the overall effects of *Cannabis*. It acts as an α2-adrenergic receptor agonist, 5-HT1A receptor antagonist, and CB1 receptor antagonist. [31] It also binds to the CB2 receptor. [31]

Tetrahydrocannabivarin (THCV) is prevalent in certain central Asian and southern African strains of *Cannabis*. It is an antagonist of THC at CB1 receptors and attenuates the psychoactive effects of THC.

Cannabidivarin (CBDV) is usually a minor constituent of the cannabinoid profile.

Cannabichromene (CBC) is non-psychoactive and does not affect the psychoactivity of THC. More common in tropical *Cannabis* varieties. Effects include anti-inflammatory and analgesic.

In addition to cannabinoids, *Cannabis* plants produce terpenes, a diverse group of organic hydrocarbons that are the building blocks of the cannabinoids.

Over 100 different terpenes have been identified in the *Cannabis* plant, and every strain tends toward a unique terpene type and composition. The terpenes act synergistically with the cannabinoids to provide a therapeutic effect. Examples of some common terpenes found in *Cannabis* include:

Borneol-menthol, camphor, pine, woody. Can be easily converted into menthol. It is considered a "calming sedative" in Chinese medicine. It is directed for fatigue, recovery from illness and stress.

Caryophyllene—spicy, sweet, woody, clove, camphor, peppery. It binds weakly to CB2 receptor. As a topical it is one of the constituents of an anti-inflammatory and analgesic treatment for toothache. In high amounts, it's a calcium and potassium ion channel blocker. As a result, it impedes the pressure exerted by heart muscles.

Cineole/Eucalyptol—spicy, camphor, refreshing, minty. It is used to increase circulation, pain relief and easily crosses the blood-brain-barrier to trigger fast olfactory reaction.

Delta3Carene—sweet, pine, cedar, woodsy, pungent. In aroma therapy, cypress oil, high in D-3-carene, is used to dry excess fluids, tears, running noses, excess menstrual flow and perspiration.

Limonene—citrus (orange, tangerine, lemon, and grapefruit), rosemary, juniper, peppermint. Repulsive to predators. Found in the rinds of many fruits and flowers. With the presence of other certain terpenes, Limonene can be an anti-bacterial, anti-fungal, anti-depressant and anti-carcinogen. It can synergistically promote the absorption of other terpenes by quickly penetrating cell membranes. The result can be increased systolic blood pressure.

Linolool—floral (spring flowers), lily, citrus and candied spice. Possesses anti-anxiety and sedative properties.

Myrcene—clove like, earthy, green-vegetative, citrus, fruity with tropical mango and minty nuances. The most prevalent terpene found in most varieties of marijuana. It's a building block for menthol, citronella, and geraniol. It possesses antimicrobial, antiseptic, analgesic, antioxidant, anti-carcinogen, anti depressant, anti-inflammatory, and muscle relaxing effects. Myrcene affects the permeability of the cell membranes, allowing more THC to reach brain cells.

Pinene—Alpha: pine needles, rosemary Beta: dill, parsley, rosemary, basil, yarrow, rose, hops, the familiar odor associated with pine trees and their resins. Pinene can increase mental focus and energy, as well as act as an expectorant, bronchodilator, and topical antiseptic. It easily crosses the blood-brain barrier where it inhibits activity of acetylcholinesterase, which destroys acetylcholine, an information transfer molecule, resulting in better memory. It may counteract THC's activity, which leads to low acetylcholine levels.

Pulegone-—mint, camphor, rosemary, candy. Pulegone is an acetylcholinesterase inhibitor. That is, it stops the action of the protein that destroys acetylcholine, which is used by the brain to store memories.

In various aspects the invention provides *Cannabis* extracts with predefined ratios of cannabinoids. Standard conditions for cannabinoid assays, and methods of calculating cannabinoid content (as %) are well known in the art.

The extracts are mixture of at least 95% total cannabinoids and include terpenes and/or flavonoids. Preferably the extracts contains a mixture of at least cannabinoids four cannabinoid such as tetrahydrocannabinolic acid (THCa), cannabidiolic acid (CBDa), cannabinolic acid (CBNa) cannabichromenic acid (CBCa), tetrahydrocannabinol (THC), cannabinol (CBN), cannabidiol (CBD) and cannabichromene (CBC).

In some embodiments the extract contains THCa and CBDa and at least two cannabinoids selected from CBNa, CBCa, THC, CBN and CBC. In other embodiments the extract includes THC, CBN, CBC and CBD. In further embodiments the extract includes THCa, CBDa, CBNa and CBCa. In other embodiments the extract includes THCa, CBDa, THC, CBN, and CBC.

The terpene and/or flavonoids in the extract include for example, terpene is linalool, 1,8-cineole (eucalyptol), α-pinene, terpineol-4-ol, p-cymene, bomeol, Δ-3-carene, β-sitosterol, β-myrcene, β-caryophyllene.d-limonene, cannflavin A, apigenin, quercetin or pulegone.

The extracts of the invention may be formulated with one or more pharmaceutically acceptable carriers, diluents or excipients or deposited on a pharmaceutically acceptable surface for vaporisation in order to produce pharmaceutical formulations containing cannabinoids as the pharmaceutically active agents.

Therefore, in a further aspect the invention provides a method of making a pharmaceutical composition comprising, as an active agent, a substance which is an extract from at least one *Cannabis* plant variety.

Separate extracts may be prepared from single *Cannabis* plant varieties having differing cannabinoid content (e.g. high THC and high CBD plants) and then mixed or blended together prior to formulation to produce the final pharmaceutical composition. This approach is preferred if, for example, it is desired to achieve a defined ratio by weight of individual cannabinoids in the final formulation. Alternatively, plant material from one or more *Cannabis* plant varieties of defined cannabinoid content may be mixed together prior to extraction of a single botanical drug substance having the desired cannabinoid content, which may then be formulated into a final pharmaceutical composition.

The extract may be formulated with any convenient pharmaceutically acceptable diluents, carriers or excipients to produce a pharmaceutical composition. The choice of diluents, carriers or excipients will depend on the desired dosage form, which may in turn be dependent on the intended route of administration to a patient. Preferred dosage forms include, liquid dosage forms for administration via pump-action or aerosol sprays, tablets, pastilles, gels, capsules, suppositories, powders, etc. and vaporizers. Such dosage forms may be prepared in accordance with standard principles of pharmaceutical formulation, known to those skilled in the art.

Liquid formulations are particularly preferred. A particularly preferred formulation for administration of cannabinoids, though not intended to be limiting to the invention, is a liquid formulation of the extracts according to the invention infused with a medium chain triglyceride (MCT). The MCT suitable for human consumption. The MCT may be composed of any combinations of C-6; C-8; C-10:C12 fatty acids. For example, the MCT is composed of 97%:3% C-8:C10;C-12 fatty acids (e.g., NEOBEE 895). Preferably the pH of the formulation is at least pH 8.0. The formulations are suitable for oral, sublingual, buccal, or topical administration. When used for sublingual administration the formulation optionally comprises a sweetener such as *stevia* extract and or a flavoring such as for example lemon oil, orange oil or both.

A preferred formulation includes a cannabinoid mixture where THCa is greater than or equal to 95%; a CBDa is less than 1%; CBNa is less than 3%; and CBCa is less than 1%. In some aspects the formulation further includes d-limonene, linalool, 1,8-cineole (eucalyptol), α-pinene, terpineol-4-ol, p-cymene, borneol, Δ-3-carene, β-sitosterol, cannflavin A, apigenin, and quercetin. This preferred formulation is referred to herein as PRANA 1.

Another preferred formulation includes a cannabinoid mixture where the THCa is less than or equal to 35%; CBDa is greater than or equal to 60%;THC is less than 1%; CBN is less than 1%; and CBC is less than 1%. In some aspects the formulation further includes d-limonene, linalool, 1,8-cineole (eucalyptol), α-pinene, terpineol-4-ol, p-cymene, bomeol, Δ-3-carene, β-sitosterol, cannflavin A, apigenin, and quercetin. This preferred formulation is referred to herein as PRANA 2.

In yet another preferred embodiment the formulation includes a cannabinoid mixture where the THCa is greater than or equal to 40%; CBDa is greater than or equal to 40%; THC is less than 1%; CBN is less than 1%; and CBC is less than 1%. In some aspects the formulation further includes β-myrcene, β-caryophyllene, pulegone, α-terpineol, β-sitosterol, cannflavin A, apigenin, and quercetin. This preferred formulation is referred to herein as PRANA 3.

In a further embodiment the formulation includes a cannabinoid mixture THC is less than or equal to 9%; CBD is greater than or equal to 40%; CBN is greater than or equal to 40%; and CBS is less than 1%. In some aspects the formulation further includes β-myrcene, β-caryophyllene, pulegone, α-terpineol, β-sitosterol, cannflavin A, apigenin, and quercetin. This preferred formulation is referred to herein as PRANA 4.

The extract is formulated for oral use (e.g. capsules) in dosage forms that provide 5 mg, 10 mg, 20 mg, or 50 mg of total cannabinoids per dose. For sublingual use, the extract is formulated to provide 0.5, 1 mg, or 2 mg, per drop.

In some applications, the patient may find it advantageous to activate (i.e., decarboxylate) the inactive (i.e. carboxylic acid form) cannabinoids in the extracts and formulations of the invention. The inactive cannabinoids (e.g., THCa and CBDa) of the extracts and formulation of the invention can be converted to active cannabinoids (THC and CBD) by heating the extracts and formulation at a temperature above 160° F. For example, a vessel containing the extracts and formulations of the invention are placed in boiling water (212° F.) for about 30 minutes.

According the invention further contemplates extracts and formulations thereof having the same ratio of cannabinoids as PRANA 1, PRANA 2 and PRANA3 where the THA and the CBD is in its activated decarboxylated form.

The methods of the invention may be used to prepare a cannabinoid-rich extract from *Cannabis* plant material. The method includes providing fresh or live *Cannabis* plant material; extracting the cannabinoids from the fresh or live plant material to produce a first extract; winterizing the first to produce a winterized extract and purging the winterized extract to produce a *Cannabis* extract. Optionally, the method includes decarboxylating the phytocannabinoids prior the extraction step.

Decarboxylation of cannabinoid acids is a function of time and temperature, thus at higher temperatures a shorter period of time will be taken for complete decarboxylation of a given amount of cannabinoid acid. In selecting appropriate conditions for decarboxylation consideration must, however, be given to minimising thermal degradation of the desirable, pharmacological cannabinoids into undesirable degradation products, particularly thermal degradation of THC to cannabinol (CBN). Preferably, decarboxylation is carried out in a multi-step heating process. For example, Phytocannabinoids are decarboxylated for example by heating the dried plant material at a temperature of about 221° F. for at least 15 minutes followed by heating at about 284° F. for at least 45 minutes. Other suitable methods of decarboxylating phytocannabinoids known in the art may be used.

In some aspects resultant *Cannabis* extract is heated at 284° F. for at about 45-74 minutes followed by heating at about 293° F. for at least about 55-90 minutes.

The *Cannabis* plant material consists of flowers or flowers and leaves. Preferably, the *Cannabis* plant material is frozen at a temperature between at least −10° F. to −50° F. for at least 36 hours prior to being dried.

The *Cannabis* plant material has been propagated from a single seed source or a tissue culture or clone with specific ratios of cannabinoids.

Any suitable method for extraction known in the art may be used. For example extraction is hydrocarbon extraction, supercritical $CO_2$ or NEOBEE 896 MCT.

The first extract may be winterizing by any method known in the art. For example the first extract is winterized by comprises adding cold ethanol or by storing the first extract at temperature of about −20° F. to about −75° F. for about 48 hours. Winterization produces a waxy precipitate. The waxy precipitate is removed by filtration. Optionally, the winterized extract through activated charcoal.

In some aspects the *Cannabis* plant material is derived from a *Cannabis* strain having a minimum of 15% THC and less that 1% CBD. In other aspects the *Cannabis* plant material is derived from *Cannabis* strains having a minimum of 10% CBD and less than 10% THC. For example the *Cannabis* plant material is derived from Sour Tsunami× Catatonic Sour Tsunami×Sour Tsunami, Sour Tsunami, Harlequin, R4 or ACDC strains. In other embodiments the *Cannabis* plant material is derived from CBD1, Sour Pineapple, CBD Diesel, Harlequin, ACDC or R4. In yet another embodiment the *Cannabis* plant material is derived from Sour Tsunami×Catatonic, Sour Tsunami×Sour Tsunami, Sour Tsunami, Harlequin, R4, Swiss Gold, ACDC, CBD1, Sour Pineapple, or CBD Diesel.

The invention also provides a method for preparing *Cannabis* juice comprising blanching fresh *Cannabis* leaves obtained from a *Cannabis* plant in the vegetative stage in cold water; juicing the leaves in a cold press juicer or masticating juicer; filtering the juice through a filter to remove particulates. Optionally, the juice freeze dried. The juicer is a cold press juicer or a masticating juicer. In some aspects the juice further includes *Cannabis* juice obtained from *Cannabis* flowers, *Cannabis* roots or both.

The juice of raw *Cannabis* provides unique healing benefits. Plant chemicals known as cannabinoid acids such as CBD-acids, and THC-acids break down quickly after harvest, so these compounds are not available in traditional preparations such as cooked 'medibles', smoking, or vaporizing The healing benefits of cannabinoid-acids are only present for a short period of time before the chemicals break down, so juicing needs to be done quickly after harvest. Fan leaves should make up the majority of the juice, and adding a small amount of *Cannabis* flowers can be beneficial.

*Cannabis* extracts and juice have wide-ranging beneficial effects on a number of medical conditions.

Chronic pain, paralysis, neuropathy, Crohn's Disease, inflammatory bowel disorders (IBS and IBD), glaucoma, PTSD, anxiety, seizures, epilepsy, autoimmune disorders, autism, tumors, and cancer have all been shown by several studies to be controlled by use of *Cannabis*. In addition, nausea and vomiting that are unresponsive to other medications have been shown to be helped through the use of *Cannabis*. Dependency on opiates have also been shown to be controlled by the use of *Cannabis*

Accordingly the invention also includes methods of alleviating a symptom associated with anxiety, post-traumatic stress disorder, chronic pain, or opiate dependency, paralysis, neuropathy, Crohn's disease, inflammatory bowel disorders, glaucoma, seizures, epilepsy, autism, or cancer comprising administering to a subject any one of the formulation according to the invention. In some embodiments the subject receives both a formulation containing a *Cannabis* extract and raw *Cannabis* in the form of a juice.

In some embodiments the formulation are administered four times daily. For example, the formulations are administered in the morning, afternoon, evening and at bedtime. The formulations are administered such that the ratio of cannabinoids are different depending upon the time of day administered. For example, formulations containing lower amounts of THC (and higher amounts of THCa) are administered during waking hours of the day. Whereas, formulations containing higher amounts of THC (and lower amounts of THCa) are administered prior to bedtime. Exemplary day time formulations include a cannabinoid mixture where THCa is greater than or equal to 95%; a CBDa is less than 1%; CBNa is less than 3%; and CBCa is less than 1%; a cannabinoid mixture where the THCa is less than or equal to 35%; CBDa is greater than or equal to 60%;THC is less than 1%; CBN is less than 1%; and CBC is less than 1%; or a cannabinoid mixture where the THCa is greater than or equal to 40%; CBDa is greater than or equal to 40%; THC is less than 1%; CBN is less than 1%; and CBC is less than 1%. An exemplary bedtime formulation includes a cannabinoid mixture THC is less than or equal to 9%; CBD is greater than or equal to 40%; CBN is greater than or equal to 40%; and CBS is less than 1%.

Preferably a formulation including a cannabinoid mixture where THCa is greater than or equal to 95%; a CBDa is less than 1%; CBNa is less than 3%; and CBCa is less than 1% is administered in the morning. Preferably a cannabinoid mixture where the THCa is less than or equal to 35%; CBDa is greater than or equal to 60%;THC is less than 1%; CBN is less than 1%; and CBC is less than 1% is administered in the afternoon. Preferably, a cannabinoid mixture where the THCa is greater than or equal to 40%; CBDa is greater than or equal to 40%; THC is less than 1%; CBN is less than 1%; and CBC is less than 1% is administered in the evening.

In various aspects the method of the invention include administering the cannabinoids containing compounds by employing an escalating dosing regimen where the total amount of cannabinoids are increased over time. For example, the amount of cannabinoids administered is increased week by week until a certain saturation point that is based on response, weight, and monthly-quarterly test results. To treat opioid dependency, opiates are gradually replaced cannabinoids.

In a preferred method cancer is treated by administering to a subject a total daily doses of:

a. 20 mg of cannabinoid extract and 50 mg of raw *Cannabis* juice for seven days;

b. 40 mg of cannabinoid extract and 50 mg of raw *Cannabis* juice for seven days;

c. 80 mg of cannabinoid extract and 50 mg of raw *Cannabis* juice for seven days;

d. 120 mg of cannabinoid extract and 50 mg of raw *Cannabis* juice for seven days; and e. 160 mg of cannabinoid extract and 100 mg of raw *Cannabis* juice for seven days.

In some embodiments, this dosing regimen is followed by administering the subject a total daily dose of 200 mg cannabinoid extract and 100 mg of raw *Cannabis* juice every day thereafter. In another embodiment this dosing regimen is followed by administering the subject 200 mg of cannabinoid extract and 100 mg of raw *Cannabis* juice for seven days; and 400 mg of cannabinoid extract and 100 mg of raw *Cannabis* juice every day thereafter.

EXAMPLES

Example 1: Preparation & Storage of *Cannabis*

Fresh *Cannabis* plant material (flowers/flower leaves) is harvested from plants propagated from cuttings taken from the mother plants, originating from a single seed source or tissue culture with specific starting ratio's of cannabinoids

*Cannabis* Plant material (flowers/flower leaves) is stored in a fresh frozen state immediately after harvesting.

Preferably the plant material is flash frozen for 10 minutes at a temperature between –10° F. and –50° F. The plant material is stored in vacuum seal bags for a minimum of 36 hrs prior to extraction. The starting *Cannabis* plant material is extracted at a 90% cannabinoid and/or phytocannabinoid concentrated form.

Example 2: Extraction of Inactive Cannabinoids

*Cannabis* flowers stored in a flash frozen state (see Example 1), and gently spread apart on curing screens while still in a frozen state. Gently break apart and spread the fresh frozen plant material into small sized pieces less than 0.7 inches on a 160u-220u screen to be air dried out.

The plant material (inactive plant matter) is placed in a stainless steel cylinder inside a closed loop hydrocarbon extraction machine such as the Emotek Obe Dos, or equal supercritical $CO_2$ extraction equipment/methods that meet these specific requirements.

Liquid hydrocarbon (99%) is run thru the product and held under pressure of (45 pounds of pressure) for approximately 45 min at a temperature –20° F. Fahrenheit to –75° F.

The result material is winterized to remove inert waxy material. Winterization is accomplished by applying a secondary gas to the liquid hydrocarbon; a cold ethanol wash that is filtered out, or by storing the extract solution at –20° F. to –75° F. for approximately 48 hrs. The resultant waxy precipitate is removed by filtration through a twenty μm membrane and passed through activated charcoal.

Finally, the extract is purged under a vacuum pressurized unit Across International Digital Vacuum Drying Oven with a solvent rated recovery pump with a min ½ hp 3425 rip oil-less compressor for approximately 48 hrs.

The final product is removed and stored in amber glass storage containers without light exposure and stored at temps below 40° F. until needed for formulation of products.

Example 3: Extraction of Active Cannabinoids

*Cannabis* flowers are air dried as in Example 2. Once the *Cannabis* flowers are air dried the *Cannabis* plant material is placed in a scientific sterile containment oven for 15 min @ 221° F. degrees, and again at 284° F. degrees for 45 min. The process in order decarboxylates the phytocannabinoids. Once the *Cannabis* plant material has been decarboxylated it is extracted in an ACTIVE The fresh *Cannabis* plant material (ACTIVE plant material) is placed in a stainless steel cylinder inside a closed loop hydrocarbon extraction Liquid hydrocarbon (99%) is run thru the product and held under pressure of (45 pounds of pressure) for approximately 45 min at a temperature –20° F. Fahrenheit to –75° F.

The result material is winterized to remove inert waxy material. Winterization is accomplished by applying a secondary gas to the liquid hydrocarbon; a cold ethanol wash that is filtered out, or by storing the extract solution at –20° F. to –75° F. for approximately 48 hrs. The resultant waxy precipitate is removed by filtration through a twenty μm membrane and passed through activated charcoal.

Finally, the extract is purged under a vacuum pressurized unit Across International Digital Vacuum Drying Oven with a solvent rated recovery pump with a min ½ hp 3425 rip oil-less compressor for approximately 48 hrs.

The resultant decarboxylated CBD:THC oil is converted to CBD:CBN (defined as >90% CBD:THC) oil by heating the oil at 284° F. for 45-75 minutes, and a second temperature at 293° F. for 55 min-90 min.

The final product is removed and stored in amber glass storage containers without light exposure and stored at temps below 40° F. until needed for formulation of products.

Example 3: Extraction Using Neobee 895 Mct

Start with cured and dried *Cannabis* flowers, flower rosin, hash rosin, hashish, or kif with specific starting ratio's of cannabinoids 1:1, 2:1, 3:1, 4:1, 8:1, 18:1, 20:1, 30:1, 50:1, 70:1. *Cannabis* flowers should be dried out with a moisture content of below 3% and gently broken apart into small sized pieces less then 0.7 inches, or finely milled into 2 mm to 3 mm sized pieces. *Cannabis* flowers, flower rosin, hash rosin, hashish, or kif are combined with NEOBEE 895 MCT. The ratio of *Cannabis* to MCT is determined based on the starting material, test results, ratio's, and desired mg per ml outcome. Example 50 g of 20% *Cannabis* flowers combined with 100 ml of MCT oil. The MCT Oil and starting *Cannabis* material is heated together in a brewer, double boiler, or on a heat plate at 41 Celsius/106 Fahrenheit for a minimum of 3 hrs in order to extract and infuse the desired cannabinoids into the MCT oil. The oil is strained thru a 15 micron stainless steel filter, or silk screen to separate the *Cannabis* content from the oil. Utilizing a Buchner funnel and 5 micron filtration system under vacuum will provide the best results for flirtation. The soaked *Cannabis* content is pressed to remove all remaining oil, filtered, and added back to the concentrated infused THCa and/or CBDa NEOBEE 895 MCT mixture. This initial mixture is considered a INACTIVE state since the cannabinoids are still in the acid forms of THCa and/or CBDa. The infused *Cannabis* and NEOBEE 895 MCT oil can be heated at 105 Celsius/221 Fahrenheit for 15 min, and repeated at 140Celsius/284

Fahrenheit 45 min −120 min to ACTIVATE the phytocannabinoids into THC and/or CBD. Decarboxylate *Cannabis* flowers, flower rosin, hash rosin, hasish, or kif THC, or CBN, can also be combined to the NEOBEE 895 MCT and heated together at 41 Celsius/106 Fahrenheit for a minimum of 3 hrs in order to infuse the ACTIVE content into the MCT oil. This process is used to create all products with specific ratio's and milligram to milliliter dosages for capsules, sublingual's, topical, transdermal, etc.

Example 4:Flower & Hash Rosin Extraction

*Cannabis* flowers are cured until moisture is below 10%. Once the *Cannabis* flowers are air dried the *Cannabis* plant material is placed in a stainless steel, or nylon silk screen sleeves with a micron ratings ranging including 15u, 25u, 90u, and 120u. Desired micron rating is used based on the starting material flower vs separated trichome heads only known as bubble hash or kif. The flowers, hash, or kif in these sleeves are placed between PTFE 3×flourmer coated sheets, or non-stick parchment paper. The sheets are a min of 2×wider then the nylon or stainless steel screens to collect the extracted cannabinoid oils and resin. A mechanical heat platen press is used with min pressure of 2500 psi with heat applied at ranges between 100-300 degree's for a range of 4 seconds to 3 min depending on the desired out come. This process mechanically separates the cannabinoids and terpenes present in the raw *Cannabis* flowers with concentrations of THCa, THC, CBDa, CBD, CBGa, CBG, CBN, CBL. The resin is collected from the PTFE or non stick parchment paper, weighed, and stored in a plastic seal bag or glass pyrex at temperatures of 32 degrees Fahrenheit or below. This type of mechanically separated *Cannabis* resin and extract is later combined with NEOBEE 895 MCT to make desired formulations, ratio's, and concentrations for the various delivery methods described in this document i.e. capsule, topical, transdermal, sublingual.

Example 5: Preparation of Raw Cannabinoids

Plants with high CBD content are best for juicing as they contain more CBD-acids than non-CBD producing strains.
Process:
1. We remove ONLY fresh *Cannabis* leaves during vegetation NOT during the flowering cycle.
2. Leaves are blanched in cold water for cleaning
3. Leaves are then juiced using a cold press juicer or commercial masticating juice
4. The juice is filtered thru a stainless steel filter to remove any particulates.
5. Juice is immediately poured into 1 oz containers or 10 oz containers and freeze-dried at −50° F. degrees.
6. Freeze-dried *Cannabis* juice can be used in capsule form, packets, or infused with a medical food.

Example 6: Formulation of *Cannabis* Extracts

Mix 1 gram of *Cannabis* oil produced by the above methods with a min of 95% total cannabinoid concentration per 40 ml of NEOBEE 895 for approximately 24 hrs at a temperature under 90° F. but not lower than 70° F. without exposure to light. The resultant infusion is mixed with NEOBEE 895 to produce capsules at 5 mg, 10 mg, 20 mg, and 50 mg total cannabinoids. For subligual formulations 0.5 g or 350 mg of the resultant infusion is combined with 9 ml of NEOBEE 895 and 1 ml of natural sweeteners and flavor additives. (*stevia*, truvia, xyotol, lemon, orange)

Example 7: Exemplary Stacking Protocol for Cancer/Tumor Treatment and Management Week #1
Morning:
+Frozen ¼ ounce of proprietary blend of Fresh Frozen Raw *Cannabis* Juice (50 mg Raw) or Powdered Raw *Cannabis* Juice added to apple juice, super smoothie, or anti-inflammatory juice beverage.
+5 mg Prana P1 Capsules
Afternoon:
+5 mg Prana P2 Capsules
Dinner:
+5 mg Prana P3 Capsules
Bedtime: (30 min Prior)
+5 mg Prana P4 Capsules
Total Cannabinoids Absorbed Daily: 20 Mg+50 Mg Raw
Week #2
Morning:
+Frozen ¼ ounce of proprietary blend of Fresh Frozen Raw *Cannabis* Juice (50 mg Raw) or Powdered Raw *Cannabis* Juice added to apple juice, super smoothie, or anti-inflammatory juice beverage.
+10 mg Prana P1 Capsules
Afternoon:
+10 mg Prana P2 Capsules
Dinner:
+10 mg Prana P3 Capsules
Bedtime: (30 min Prior)
+10 mg Prana P4 Capsules
Total Cannabinoids Absorbed Daily: 40 Mg+50 Mg Raw
Week #3 (Min Holding Dose)
Morning:
+Frozen ¼ ounce of proprietary blend of Fresh Frozen Raw *Cannabis* Juice (50 mg Raw) or Powdered Raw *Cannabis* Juice added to apple juice, super smoothie, or anti-inflammatory juice beverage.
+20 mg Prana P1 Capsules
Afternoon:
+20 mg Prana P2 Capsules
Dinner:
+20 mg Prana P3 Capsules
Bedtime: (30 min Prior)
+20 mg Prana P4 Capsules
Total Cannabinoids Absorbed Daily: 80 mg+50 mg Raw
Week #4
Morning:
+Frozen ¼ ounce of proprietary blend of Fresh Frozen Raw *Cannabis* Juice (50 mg Raw) or Powdered Raw *Cannabis* Juice added to apple juice, super smoothie, or anti-inflammatory juice beverage.
+30 mg Prana P1 Capsules
Afternoon:
+30 mg Prana P2 Capsules
Dinner:
+30 mg Prana P3 Capsules
Bedtime: (30 min Prior)
+30 mg Prana P4 Capsules
Total Cannabinoids Absorbed Daily: 120 Mg+50 Mg Raw
Week #5
Morning:
+Frozen 0.5 ounce of proprietary blend of Fresh Frozen Raw *Cannabis* Juice (100 mg Raw) or Powdered Raw 15 16

*Cannabis* Juice added to apple juice, super smoothie, or anti-inflammatory juice beverage.
+40 mg Prana P1 Capsules
Afternoon:
+40 mg Prana P2 Capsules
Dinner:
+40 mg Prana P3 Capsules
Bedtime: (30 min Prior)
+40 mg Prana P4 Capsules
Total Cannabinoids Absorbed Daily: 160 mg+100 mg Raw
Week #6 (Advanced Holding Dose)
Morning:
+Frozen 0.5 ounce of proprietary blend of Fresh Frozen Raw *Cannabis* Juice (100 mg Raw) or Powdered Raw *Cannabis* Juice added to apple juice, super smoothie, or anti-inflammatory juice beverage.
+50 mg Prana P1 Capsules
Afternoon:
+50 mg Prana P2 Capsules
Dinner:
+50 mg Prana P3 Capsules
Bedtime: (30 min Prior)
+50 mg Prana P4 Capsules
Total Cannabinoids Absorbed Daily: 200 Mg+100 Mg Raw
Week #7-Week #12 (Advanced Stages)
Morning:
+Frozen 0.5 ounce of proprietary blend of Fresh Frozen Raw *Cannabis* Juice (100 mg Raw) or Powdered Raw *Cannabis* Juice added to apple juice, super smoothie, or anti-inflammatory juice beverage.
+100 mg Prana P1 Capsules
Afternoon:
+100 mg Prana P2 Capsules
Dinner:
+100 mg Prana P3 Capsules
Bedtime: (30 min Prior)
+100 mg Prana P4 Capsules Example 7: Exemplary Protocol For Anxiety/Ptsd Morning
+5 mg—10 mg Prana P2 CBD AM Capsules (2:1 to 3:1, THC:CBD)
+2 mg to 4 mg Prana P4 CBD:CBN Sublingual (1:1)
Afternoon:
+2 mg to 4 mg Prana P4 CBD:CBN Sublingual (1:1)
Used when feeling anxiety or PSTD throughout the day.
After Dinner:
+5 mg—10 mg Prana P3 CBD PM Capsules (2:1 to 1:1, THCa:CBDa)
+4 mg Prana P4 CBD:CBN Sublingual (1:1)
Bedtime:
+10 mg Prana P4 CBN Capsules Example 8: Exemplary Protocol for Chronic Pain Morning:
+5 mg Prana P2 CBD AM Capsules (2:1 to 3:1, THC: CBD)
+2 mg to 4 mg Prana P1 THCa Sublingual
Afternoon:
+5 mg Prana P2 CBD AM Capsules (2:1 to 3:1, THC: CBD)
+2 mg to 4 mg Prana P1 THCa Sublingual (As Needed)

Dinner:
+10 mg Prana P3 CBD PM Capsules (2:1 to 1:1, THCa: CBDa)
+2 mg to 4 mg Prana P1 THCa Sublingual
Bedtime:
+10 mg Prana P4 CBN Capsules Example 9: Exemplary Protocol for Opiate Dependency Note: This is a 16 week program.
Week #1 & Week #2
Morning:
+Prana P5-100 gms raw or 10 gms powder
+5 mg Prana P1 Prana Capsule
+2 mg Prana P2 CBD AM Sublingual (2:1 to 3:1, THC: CBD)
Afternoon:
+5 mg Prana P1 Prana Capsule
+2 mg Prana P2 CBD AM Sublingual (2:1 to 3:1)
Dinner:
+5 mg Prana P1 Prana Capsule
+2 mg Prana P2 CBD AM Sublingual (2:1 to 3:1)
Bedtime: (30 min Prior)
+10 mg Prana P3 CBD PM Capsules (2:1 to 1:1)
+2 mg Prana P4 Sublingual CBD:CBN (1:1)
Total Cannabinoids Daily: 31 Mg+50 Mg Raw Reduce Opiates by 10%-20%
Week #3 & Week #4
Morning:
+Prana P5-100 gms raw or 10 gms powder
+10 mg Prana P1 Capsules
+4 mg Prana P2 CBD AM Sublingual (2:1 to 3:1)
Afternoon:
+10 mg Prana P1 THCa Capsules
+4 mg Prana P2 CBD AM Sublingual (2:1 to 3:1)
Dinner:
+10 mg Prana P1 THCa Capsules
+4 mg Prana P2 CBD AM Sublingual (2:1 to 3:1)
Bedtime: (30 min Prior)
+10 mg Prana P3 CBD PM Capsules (2:1 to 1:1)
+4 mg Prana P4 Sublingual CBD:CBN (1:1)
Total Cannabinoids Absorbed Daily: 56 Mg+50 Mg Raw Reduce Opiates by 10%-20%
Week #5 & Week #6
Morning:
+Prana P5-100 gms raw or 10 gms powder
+15 mg Prana P1 THCa Capsules
+6 mg Prana P2 CBD AM Sublingual (2:1 to 3:1)
Afternoon:
+15 mg Prana P1 THCa Capsules
+6 mg Prana P2 CBD AM Sublingual (2:1 to 3:1)
Dinner:
+15 mg Prana P1 THCa Capsules
+6 mg Prana P2 CBD AM Sublingual (2:1 to 3:1)
Bedtime: (30 min Prior)
+15 mg Prana P3 CBD PM Capsules (2:1 to 1:1)
+6 mg Prana P4 Sublingual CBD:CBN (1:1)
Total Cannabinoids Absorbed Daily: 84 Mg+50 Mg Raw Reduce Opiates by 10%-20%
Week #7 & Week #8
Morning:
+Prana P5-100 gms raw or 10 gms powder
+20 mg Prana P1 Prana Capsule
+6 mg Prana P2 CBD AM Sublingual (2:1 to 3:1)

Afternoon:

+20 mg Prana P1 Prana Capsule

+6 mg Prana P2 CBD AM Sublingual (2:1 to 3:1)

Dinner:

+20 mg Prana P1 THC Capsules

+6 mg Prana P2 CBD AM Sublingual (2:1 to 3:1)

Bedtime: (30 min Prior)

+20 mg Prana P3 CBD PM Capsules (2:1 to 1:1)

+6 mg Prana P4 Sublingual CBD:CBN (1:1)

Total Cannabinoids Absorbed Daily: 104 Mg+50 Mg Raw

Reduce Opiates by 10%-20%

Week #8 & Week 9

Morning:

+Prana P5-100 gms raw or 10 gms powder

+15 mg Prana P1 Prana Capsule

+6 mg Prana P2 CBD AM Sublingual (2:1 to 3:1)

Afternoon:

+15 mg Prana P1 Prana Capsule

+6 mg Prana P2 CBD AM Sublingual (2:1 to 3:1)

Dinner:

+15 mg Prana P1 Prana Capsule

+6 mg Prana P2 CBD AM Sublingual (2:1 to 3:1)

Bedtime: (30 min Prior)

+20 mg Prana P3 CBD PM Capsules (2:1 to 1:1)

+6 mg Prana P4 Sublingual CBD:CBN (1:1)

Total Cannabinoids Absorbed Daily: 89 Mg+50 Mg Raw

Reduce Opiates by 10%-20%

Week #10 & Week #11

Morning:

+Prana P5-100 gms raw or 10 gms powder

+10 mg Prana P1 Prana Capsule

+6 mg Prana P2 CBD AM Sublingual (2:1 to 3:1)

Afternoon:

+10 mg Prana P1 Prana Capsule

+6 mg Prana P2 CBD AM Sublingual (2:1 to 3:1)

Dinner:

+10 mg Prana P1 Prana Capsule

+6 mg Prana P2 CBD AM Sublingual (2:1 to 3:1)

Bedtime: (30 min Prior)

+15 mg Prana P3 CBD PM Capsules (2:1 to 1:1)

+6 mg Prana P4 Sublingual CBD:CBN (1:1)

Total Cannabinoids Absorbed Daily: 69 Mg+50 Mg Raw

Reduce Opiates by 10%-20%

Week #12 & Week #13

Morning:

+Prana P5-100 gms raw or 10 gms powder

+5 mg Prana P1 Prana Capsule

+6 mg Prana P2 CBD AM Sublingual (2:1 to 3:1)

Afternoon:

+5 mg Prana P1 Prana Capsule

+6 mg Prana P2 CBD AM Sublingual (2:1 to 3:1)

Dinner:

+5 mg Prana P1 Prana Capsule

+6 mg Prana P2 CBD AM Sublingual (2:1 to 3:1)

Bedtime: (30 min Prior)

+10 mg Prana P3 CBD PM Capsules (2:1 to 1:1)

+6 mg Prana P4 Sublingual CBD:CBN (1:1)

Total Cannabinoids Absorbed Daily: 49 Mg+50 Mg Raw

Reduce Opiates by 10%-20%

Week #14 & Week #15

Morning:

+Prana P5-100 gms raw or 10 gms powder

+4 mg Prana P1 THCa Sublingual

+5 mg Prana P2 CBD AM Capsule (2:1 to 3:1)

Afternoon:

+4 mg Prana P1 THCa Sublingual

+5 mg Prana P2 CBD AM Capsule (2:1 to 3:1)

Dinner:

+4 mg Prana P1 THCa Sublingual

+5 mg Prana P2 CBD AM Capsule (2:1 to 3:1)

Bedtime: (30 min Prior)

+10 mg Prana P3 CBD PM Capsules (2:1 to 1:1)

+4 mg Prana P4 Sublingual CBD:CBN (1:1)

Total Cannabinoids Absorbed Daily: 41 Mg+50 Mg Raw

Opiates should be Reduced by 80-90%

Week #16+

+Every 3rd Day+Prana P5-100 gms raw or 10 gms powder

Morning:

+10 mg Prana P2 CBD AM Capsule (2:1 to 3:1)

+4 mg Prana P1 THCa Sublingual (Only As Needed for Pain)

Afternoon:

+4 mg Prana P1 THCa Sublingual (Only As Needed for Pain)

Dinner:

+10 mg Prana P3 CBD PM Capsule (2:1 to 1:1)

+4 mg Prana P1 THCa Sublingual (Only As Needed for Pain)

Bedtime: (30 min Prior)

+4 mg Prana P4 Sublingual CBD:CBN (1:1)

Total Cannabinoids Absorbed Daily: 36 Mg+25 Mg Raw

Opiates should be Reduced by 90%-100%.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A kit comprising at least one cannabinoid formulation, wherein the at least one formulation is selected from the group consisting of:

(a) a formulation wherein 95% or more of the total cannabinoids in the formulation is tetrahydrocannabinolic acid (THCa), cannabidiolic acid (CBDa) is less than 1%, cannabinolic acid (CBNa) is less than 3% and cannabichromenic acid (CBCa) is less than 1%;

(b) a formulation wherein 95% or more of the total cannabinoids in the formulation is tetrahydrocannabinol (THC), cannabidiol (CBD) is less than 1%, cannabinol (CBN) is less than 3% and cannabichromene (CBC) is less than 1%;

(c) a formulation wherein THCa is less than or equal to 35%, CBDa is greater than or equal to 60%, THC is less than 1%, CBN is less than 1% and CBC is less than 1%;

(d) a formulation wherein THCa is greater than or equal to 40%, CBDa is greater than or equal to 40%, THC is less than 1%, CBN is less than 1% and CBC is less than 1%;

(e) a formulation wherein THC is less than or equal to 35%, CBD is greater than or equal to 60%, CBN is less than 1%, and CBC is less than 1%;

(f) a formulation wherein THC is greater than or equal to 40%, CBD is greater than or equal to 40%, CBN is less than 1% and CBC is less than 1%; and (g) a formulation wherein THC is less than or equal to 9%, CBD is greater than or equal to 40%, CBN is greater than or equal to 40% and CBC is less than 1%; and wherein the cannabinoid formulation further comprises one or more terpene and/or flavonoid, wherein the cannabinoid formulation is infused in a medium chain triglyceride (MCT).

2. The kit of claim 1, wherein the MCT is composed of any combination of C-6, C-8, C-10 and C-12 fatty acids.

3. The kit of claim 1, wherein two or more of the cannabinoid formulations are administered to relieve symptoms associated with anxiety, post-traumatic stress disorder, chronic pain, opiate dependency, paralysis, neuropathy, Crohn's disease, inflammatory bowel disorders, glaucoma, seizures, epilepsy, autism, or cancer.

4. The kit of claim 1, wherein the cannabinoid formulation is a liquid.

5. The kit of claim 1, wherein the terpene comprises β-myrcene, β-caryophyllene, or d-limonene.

6. The kit of claim 1, wherein the pH of the cannabinoid formulation is at least pH 8.0.

7. A method of preparing a *Cannabis* extract comprising:
a. providing a *Cannabis* starting plant material comprising dried *Cannabis* flowers, flower rosin, hash rosin, hashish or kif, wherein the *Cannabis* flowers have a moisture content below 3%;
b. breaking apart or milling the *Cannabis* starting plant material;
c. combining the *Cannabis* starting plant material with a medium chain triglyceride (MCT) comprising NEO-BEE 895 to produce a mixture;
d. heating the mixture for at least 3 hours to extract and infuse cannabinoids into the MCT; and
e. separating the *Cannabis* starting plant material and the MCT using a filter or silk screen to produce a *Cannabis* extract.

8. The method of claim 7, further comprising decarboxylating the phytocannabinoids prior to step (c).

9. The method of claim 8, wherein the decarboxylating comprises heating the *Cannabis* starting material at a temperature of about 221° F. for at least 15 minutes followed by heating at about 284° F. for at least 45 minutes.

10. The method of claim 7, further comprising heating the *Cannabis* extract at 284° F. for at about 45-74 minutes followed by heating at about 293° F. for at least about 55-90 minutes.

11. The method of claim 7, wherein the *Cannabis* plant material has been propagated from a single seed source or a tissue culture with specific ratios of cannabinoids.

12. The method of claim 7, wherein the *Cannabis* plant material is derived from a *Cannabis* strain having a minimum of 15% THC and less that 1% CBD.

13. The method of claim 7, wherein the *Cannabis* plant material is derived from Sour Tsunami×Catatonic, Sour Tsunami×Sour Tsunami, Sour Tsunami, Harlequin, R4, Swiss Gold, ACDC, CBD1, Sour Pineapple, or CBD Diesel.

14. The method of claim 7, wherein the *Cannabis* plant material is derived from Sour Tsunami×Catatonic, Sour Tsunami×Sour Tsunami, Sour Tsunami, Harlequin, R4 or ACDC strains.

15. The method of claim 7, wherein the *Cannabis* plant material is derived from CBD1, Sour Pineapple, CBD Diesel, Harlequin, ACDC or R4.

\* \* \* \* \*